United States Patent
Park et al.

(10) Patent No.: US 10,481,053 B2
(45) Date of Patent: Nov. 19, 2019

(54) METHOD FOR DETECTING DEFECTS OF GLASS SUBSTRATES

(71) Applicant: Samsung Display Co., Ltd., Yongin-si, Gyeonggi-do (KR)

(72) Inventors: Cheol Min Park, Hwaseong-si (KR); Jeong Woo Park, Yongin-si (KR); Seung Kim, Seongnam-si (KR); Seung Ho Kim, Asan-si (KR); Hoi Kwan Lee, Suwon-si (KR); Woo Jin Cho, Yongin-si (KR); Hee Kyun Shin, Incheon (KR); Hyun Joon Oh, Seongnam-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 26 days.

(21) Appl. No.: 15/816,943

(22) Filed: Nov. 17, 2017

(65) Prior Publication Data

US 2018/0136095 A1 May 17, 2018

(30) Foreign Application Priority Data

Nov. 17, 2016 (KR) .......................... 10-2016-0153327

(51) Int. Cl.
*G01N 1/30* (2006.01)
*G01N 21/958* (2006.01)
(Continued)

(52) U.S. Cl.
CPC .............. *G01N 1/30* (2013.01); *G01N 21/91* (2013.01); *G01N 21/958* (2013.01); *C03C 15/00* (2013.01);
(Continued)

(58) Field of Classification Search
CPC ........ G01N 1/30; G01N 21/958; G01N 23/00; C03C 15/00; C03C 23/0055; C03C 19/00;
(Continued)

(56) References Cited

U.S. PATENT DOCUMENTS 6,136,211 A * 10/2000 Qian ................. H01L 21/02071
134/21
6,501,546 B1 * 12/2002 Weiss ................... G01N 21/958
356/239.1
(Continued)

FOREIGN PATENT DOCUMENTS

JP      2000-40694 A    2/2000
JP      4558285 B2     10/2010
(Continued)

OTHER PUBLICATIONS

Iwasaki, M., et al., "Roles of oxidizing species in a nonequilibrium atmospheric-pressure pulsed remote $O_2/N_2$ plasma glass cleaning process", Journal of Applied Physics, 103, (2008), 8 pages.

*Primary Examiner* — Isiaka O Akanbi
(74) *Attorney, Agent, or Firm* — Lewis Roca Rothgerber Christie LLP (57) ABSTRACT

A method of detecting defects of a glass substrate includes cutting a glass mother substrate into a plurality of glass substrates, penetrating ions into an incision surface of the glass substrate to visualize defects of the incision surface, and photographing the defects of the incision surface to determine a bending strength of the glass substrate based on a size of the defects.

10 Claims, 7 Drawing Sheets

Cutting a glass mother substrate into a plurality of glass substrate — S100

Penetrating ions into an incision surface of the glass substrate to visualize a defect of the incision surface — S200

Photographing the defect of the incision surface to determine a bending strength of the glass substrate — S300

(51) Int. Cl.
*G01N 21/91* (2006.01)
*C03C 15/00* (2006.01)
*C03C 19/00* (2006.01)
*C03C 23/00* (2006.01)
*G02F 1/13* (2006.01)
*G02F 1/1333* (2006.01)
*H01L 51/00* (2006.01)

(52) U.S. Cl.
CPC .......... *C03C 19/00* (2013.01); *C03C 23/0055* (2013.01); *G02F 1/1303* (2013.01); *G02F 1/1309* (2013.01); *G02F 1/1333* (2013.01); *G02F 2001/133302* (2013.01); *H01L 51/0096* (2013.01)

(58) Field of Classification Search
CPC .... G02F 1/1303; G02F 1/1309; G02F 1/1333; G02F 2001/133302; H01L 51/0096
USPC ................................ 356/239.1, 237.2–237.6
See application file for complete search history.

(56) References Cited

U.S. PATENT DOCUMENTS

| | | | | |
|---|---|---|---|---|
| 8,722,189 | B2 * | 5/2014 | Fujii | ........................ C03C 3/083 428/410 |
| 9,249,049 | B2 * | 2/2016 | Fujii | ........................ C03C 3/083 |
| 10,205,478 | B2 * | 2/2019 | Fujii | ........................ C03C 3/083 |
| 2010/0288330 | A1 | 11/2010 | Riva | |
| 2011/0003619 | A1 * | 1/2011 | Fujii | ........................ C03C 3/083 455/566 |
| 2014/0083198 | A1 * | 3/2014 | Sharps | ................ G01M 5/0075 73/834 |
| 2017/0148612 | A1 * | 5/2017 | Suzuki | ................ H01L 21/3065 |

FOREIGN PATENT DOCUMENTS

| | | |
|---|---|---|
| KR | 2002-0085149 A | 11/2002 |
| KR | 10-0939424 B1 | 1/2010 |
| KR | 10-2010-0092785 A | 8/2010 |
| KR | 10-2011-0131433 A | 12/2011 |
| KR | 10-2012-0133734 A | 12/2012 |
| KR | 10-1278249 B1 | 6/2013 |
| KR | 10-2013-0072771 A | 7/2013 |
| KR | 10-2015-0063581 A | 6/2015 |
| WO | WO 2006/087213 A2 | 8/2006 |
| WO | WO 2009/092453 A2 | 7/2009 |
| WO | WO 2012/077683 A1 | 6/2012 |
| WO | WO-2016104754 A1 * | 6/2016 ......... H01L 21/3065 |

* cited by examiner

| | Experimental example Before plasma processing | Experimental example After plasma processing | Comparative example After plasma processing |
|---|---|---|---|
| Image | | | |
| Four axes Bending strength average | 120MPa | 117MPa | 85MPa |
| Plasma Power, Gas | | RF Power : 240Watt<br>Reaction Gas : Ar, He ($O_2$, $H_2$)<br>Etching Gas : $NF_3$, ($CF_4$) | RF Power : 240Watt<br>Reaction Gas : Ar, He ($O_2$, $H_2$)<br>Etching Gas : $NF_3$, ($CF_4$) |
| Defect Size | 100㎛(20%) | 250㎛(50%) | 500㎛(100%) |
| Result | Spec' In | Spec' In | Spec' Out |

METHOD FOR DETECTING DEFECTS OF GLASS SUBSTRATES

CROSS-REFERENCE TO RELATED APPLICATIONS

This application claims priority to and the benefit of Korean Patent Application No. 10-2016-0153327 filed in the Korean Intellectual Property Office on Nov. 17, 2016, the entire content of which is incorporated herein by reference.

BACKGROUND

1. Field

One or more aspects of example embodiments of the present disclosure relate to a method for detecting defects of a glass substrate.

2. Description of the Related Art

In general, a display device, such as an organic light emitting diode display, a liquid crystal display, etc., includes a glass substrate as a substrate.

The glass substrate is cut from a glass mother substrate, which is used to manufacture a plurality of glass substrates.

Defects, such as a hole, a groove, a crack, etc., may remain on or in an incision surface of the glass substrates cut from the glass mother substrate.

When a large-sized defect exists on or in the incision surface of the glass substrate, there is a problem that bending strength of the glass substrate decreases (i.e., relative to a glass substrate that does not have such defects).

The above information disclosed in this Background section is only for enhancing understanding of the background of the described technology, and therefore it may contain information that does not form prior art.

SUMMARY

Aspects of embodiments of the present disclosure provide a method for detecting defects of a glass substrate for determining bending strength of the glass substrate based on the size of the defects of the glass substrate.

Aspects of embodiments provide a method for detecting defects of a glass substrate, including cutting a glass mother substrate into a plurality of glass substrates, penetrating ions into an incision surface of the glass substrate to visualize defects of the incision surface, and photographing the defects of the incision surface to determine a bending strength of the glass substrate based on a size of the defects.

The step of visualizing the defect of the incision surface may include performing plasma processing on the incision surface.

The plasma processing may be performed by using a mixture of a reaction gas and an etching gas.

The reaction gas may include at least one among argon (Ar), helium (He), oxygen ($O_2$), and hydrogen ($H_2$).

The etching gas may include at least one of nitrogen trifluoride ($NF_3$) and carbon tetrafluoride ($CF_4$).

The plasma processing may be performed for between 10 seconds to 10 minutes.

The plasma processing may be performed after the plurality of glass substrates are cut from the glass mother substrate and stacked together.

The detecting method may further include grinding the incision surface of the glass substrate after being cut from the glass mother substrate.

The step of visualizing the defect of the incision surface may be performed by blackening the defects through the ions.

The step of determining the bending strength of the glass substrate based on the size of the defects may be performed by using a photographed image of the incision surface.

BRIEF DESCRIPTION OF THE DRAWINGS

The above and other features of the present disclosure will become more apparent by reference to the following detailed description when considered in conjunction with the accompanying drawings, wherein.

DETAILED DESCRIPTION

Hereinafter, example embodiments will now be described in more detail with reference to the accompanying drawings, in which like reference numbers refer to like elements throughout. The present invention, however, may be embodied in various different forms, and should not be construed as being limited to only the illustrated embodiments herein. Rather, these embodiments are provided as examples so that this disclosure will be thorough and complete, and will fully convey the aspects and features of the present invention to those skilled in the art. Accordingly, processes, elements, and techniques that are not necessary to those having ordinary skill in the art for a complete understanding of the aspects and features of the present invention may not be described. Unless otherwise noted, like reference numerals denote like elements throughout the attached drawings and the written description, and thus, descriptions thereof will not be repeated. In the drawings, the relative sizes of elements, layers, and regions may be exaggerated for clarity.

In the following description, for the purposes of explanation, numerous specific details are set forth to provide a thorough understanding of various embodiments. It is apparent, however, that various embodiments may be practiced without these specific details or with one or more equivalent arrangements. In other instances, well-known structures and devices are shown in block diagram form in order to avoid unnecessarily obscuring various embodiments.

In the drawings, thicknesses of a plurality of layers and areas are illustrated in an enlarged manner for clarity and ease of description thereof.

Spatially relative terms such as "below", "beneath", "lower", "above", "upper" and the like, may be used herein for ease of description to describe the relations between one element or component and another element or component as illustrated in the drawings. It will be understood that the spatially relative terms are intended to encompass different orientations of the device in use or operation, in addition to the orientation depicted in the drawings. For example, in the case where a device illustrated in the drawing is turned over, the device positioned "below" or "beneath" another device may be placed "above" another device. Accordingly, the example terms "below" and "under" may include both an orientation of above and below.

It will be further understood that the terms "comprises," "comprising," "includes" and/or "including," when used in this specification, specify the presence of stated features, integers, steps, operations, elements and/or components, but do not preclude the presence or addition of one or more other features, integers, steps, operations, elements, components and/or groups thereof.

As used herein, the terms "substantially," "about," "approximately" and similar terms are used as terms of approximation and not as terms of degree, and are intended to account for the inherent deviations in measured or calculated values that would be recognized by those of ordinary skill in the art. Further, these terms as used herein are inclusive of the stated value and means within an acceptable range of deviation for the particular value as determined by one of ordinary skill in the art, considering the measurement in question and the error associated with measurement of the particular quantity (i.e., the limitations of the measurement system). For example, "about" may mean within one or more standard deviations, or within ±30%, 20%, 10%, 5% of the stated value.

Unless otherwise defined, all terms used herein (including technical and scientific terms) have the same meaning as commonly understood by those skilled in the art to which this invention pertains. It will be further understood that terms, such as those defined in commonly used dictionaries, should be interpreted as having a meaning that is consistent with their meaning in the context of the relevant art and will not be interpreted in an ideal or excessively formal sense unless clearly defined in the present specification.

Further, the use of "may" when describing embodiments of the present invention refers to "one or more embodiments of the present invention." As used herein, the terms "use," "using," and "used" may be considered synonymous with the terms "utilize," "utilizing," and "utilized," respectively. Also, the term "exemplary" is intended to refer to an example or illustration.

Hereinafter, a method for detecting defects of a glass substrate according to some embodiments will be described with reference to FIG. 1 to FIG. 6.

Figure 1:
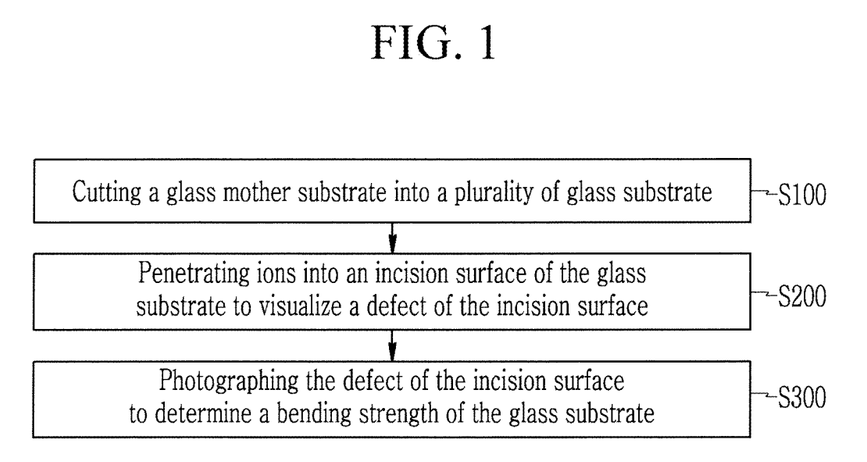
FIG. 1 is a flowchart showing a method for detecting defects of a glass substrate according to some embodiments.
Figure 2:
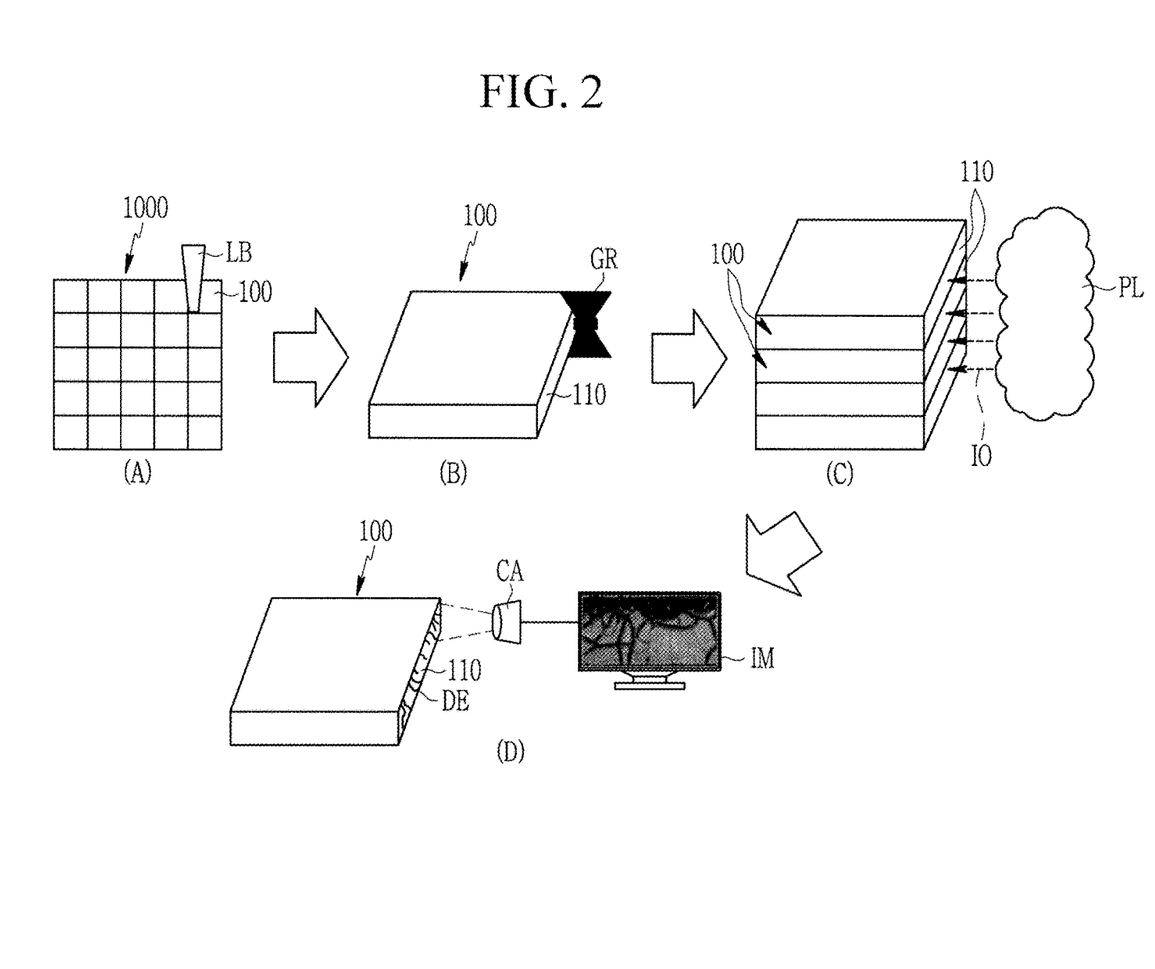
FIG. 2 is a view showing a method for detecting defects of a glass substrate according to some embodiments.

FIG. 1 is a flowchart showing a method for detecting defects of a glass substrate according to some embodiments. FIG. 2 is a view showing a method for detecting defects of a glass substrate according to some embodiments.

First, referring to FIG. 1 and detail (A) of FIG. 2, a glass mother substrate 1000 is cut into a plurality of glass substrates 100 (S100).

In more detail, the glass mother substrate 1000 having a large area is cut into the plurality of glass substrates 100 having a small area (i.e., relative to the glass mother substrate 1000) by using a cutting device such as a laser beam LB. However, the cutting device is not limited thereto or thereby. It should be appreciated that various suitable devices and/or methods known in the art for cutting glass may be used as the cutting device, as well as the laser beam LB.

Next, referring to detail (B) of FIG. 2, an incision surface 110 of the glass substrate 100 is ground (e.g., a surface of the glass substrate that has been cut by the cutting device).

In more detail, a corner of the incision surface 110 of the glass substrate 100 may be ground by using a grinder GR. In some embodiments, the process of grinding the incision surface 110 of the glass substrate 100 may be omitted.

Next, referring to detail (C) of FIG. 2, ions IO are penetrated into the incision surface 110 of the glass substrate 100 to visualize one or more defects DE of the incision surface 110 (S200).

In more detail, the plurality of glass substrates 100 may be stacked, and the ions IO are penetrated into the respective incision surfaces 110 of the plurality of glass substrates 100 to visualize one or more defects DE of the incision surfaces 110. The penetration of the ions IO into each incision surface 110 may be executed through plasma PL processing on the incision surfaces 110. That is, the defects DE of the incision surfaces 110 may be visualized through the plasma PL processing on the incision surfaces 110. In some embodiments, the ions IO may penetrate only some of the plurality of glass substrates 100 (e.g., a single glass substrate 100). Further, in some embodiments, stacking the plurality of glass substrates 100 may be omitted.

The plasma PL processing on the incision surfaces 110 may be executed by using a mixture of a reaction gas and an etching gas. Herein, the reaction gas may include at least one from among argon (Ar), helium (He), oxygen ($O_2$) and hydrogen ($H_2$). The etching gas may include at least one from among nitrogen trifluoride ($NF_3$) and carbon tetrafluoride ($CF_4$).

The plasma PL processing may be performed in a plasma reactor. The plasma reactor may include a chamber having a processing space in which the plasma processing is performed and an electrode for producing plasma of a gas positioned inside chamber (e.g., the reaction gas and etching gas mixture described above). The plasma reactor may have various disclosed structures or shapes.

The plasma PL processing on the incision surfaces 110 may be performed for a limited time, and only during a time when the ions IO penetrate into the defects DE of the incision surfaces 110. In some embodiments, the plasma PL processing may be performed for a time between 10 seconds and 10 minutes. As the plasma PL processing on the incision surfaces 110 is only performed for a limited time, the incision surfaces 110 are not etched by the plasma PL.

By the plasma (PL) processing, the defects DE of the incision surfaces 110 are visualized by the ions IO penetrating into the incision surfaces 110. For example, the defects DE formed in the incision surfaces 110, such as a hole, a groove, a crack, etc., may appear blackened (e.g., appearing as a dark color). In more detail, as the ions IO are aggregated in the defects DE formed on the incision surfaces 110, the defects DE of the incision surfaces 110 may become blackened. In some embodiments, the defects DE may be visualized as other colors by the plasma PL processing.

Next, referring to detail (D) of FIG. 2, by photographing the defects DE of the incision surface 110 of the glass substrate 100, bending strength of the glass substrate 100 is determined based on the size of the defects DE (S300).

In more detail, the incision surface 110 in which the defects DE are visualized is photographed by using a photographing device such as a camera CA. Also, the bending strength of the glass substrate 100 is determined based on the size of the defects DE displayed on the photographed image IM in which the incision surface 110 is photographed.

Figure 3A:
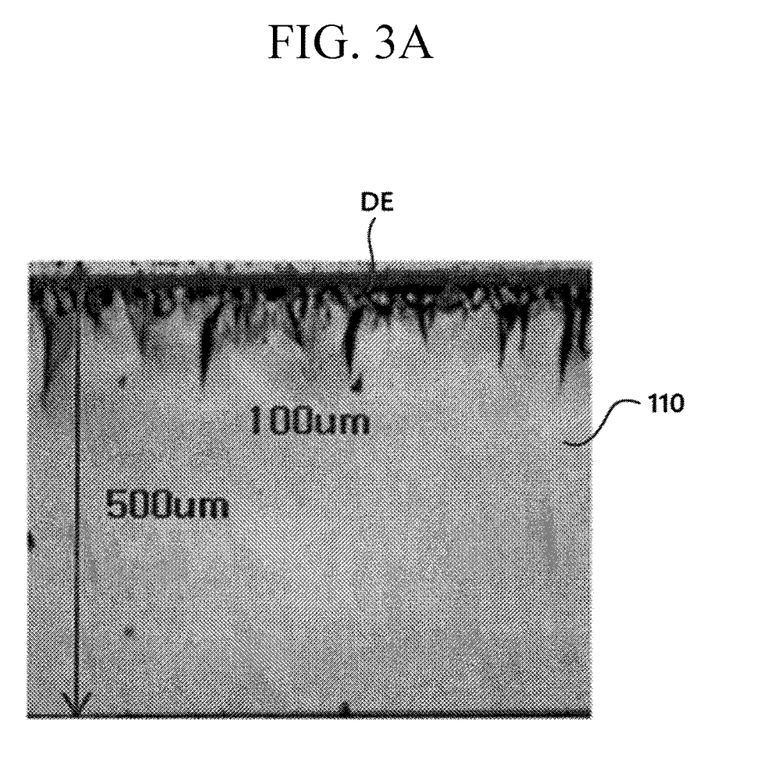
FIG. 3A and FIG. 3B are views showing an image of which an incision surface of a glass substrate is photographed according to some embodiments.
Figure 3B:
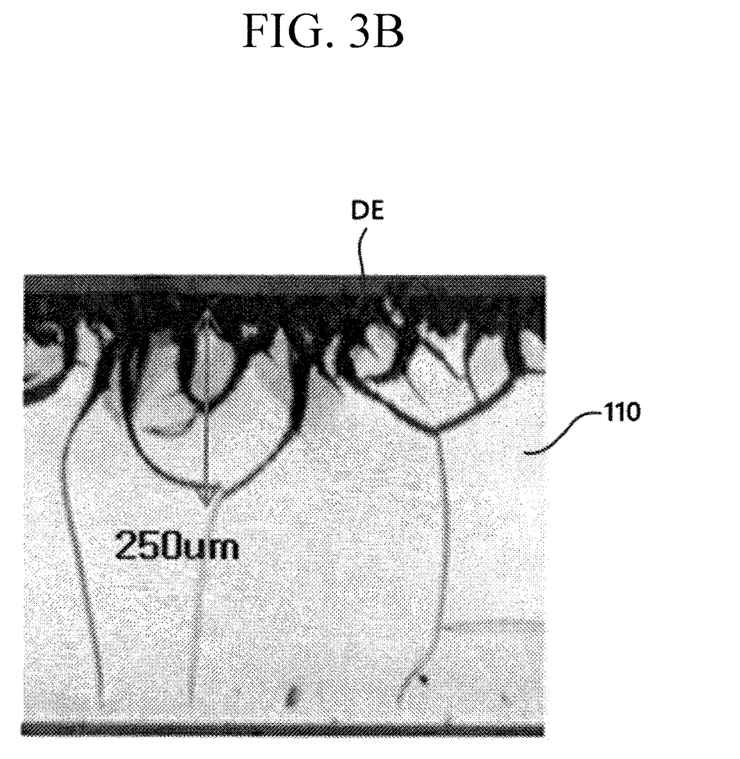

FIG. 3A and FIG. 3B show images in which the incision surface of the glass substrate is photographed according to some embodiments.

FIG. 3A is an image in which the incision surface 110 is photographed before plasma processing, and FIG. 3B is an image in which the incision surface 110 is photographed after plasma processing.

Referring to FIG. 3A, the defects DE of the incision surface 110 before plasma processing have a size (e.g., height or length) of approximately 100 micrometers or microns (µm).

Referring to FIG. 3B, the defects DE of the incision surface 110 after plasma processing is visualized by ions IO have a size of approximately 250 µm. As described above, the defects DE of the incision surface 110 before plasma processing have a size of approximately 100 µm, however the defects DE of the incision surface 110 after the plasma processing is visualized by the ions IO have a size of approximately 250 µm.

The size of the visualized defects DE of the incision surface 100 of the glass substrate 100 may be compared to a predetermined size. When the size of the defects DE of the incision surface 110 of the glass substrate 100 displayed on the image IM is less than the predetermined size, it may be determined that the bending strength of the glass substrate 100 has a desired value (e.g., the bending strength of the glass substrate 100 meets a target bending strength value). In such a case, the glass substrate 100 may be used as a substrate of the display device, such as an organic light emitting diode display, a liquid crystal display, etc.

When the size of the defects DE of the incision surface 110 of the glass substrate 100 displayed on the image IM is more than (e.g., greater than) the predetermined size, it may be determined that the bending strength of the glass substrate 100 does not have the desired value (e.g., the bending strength of the cut glass substrate 100 does not meet the target bending strength value). In such a case, the glass substrate 100 may be discarded.

In some embodiments, the predetermined size used for comparison of the defects DE of the incision surface 110 of the glass substrate 100 may be a size of 90% of the height of the incision surface 110 (e.g., extending between an upper end of the incision surface 110 to a lower end of the incision surface 110). For example, when the height of the incision surface 110 of the glass substrate 100 is 500 µm, the predetermined size used for comparison of the defects DE of the incision surface 110 of the glass substrate 100 may be 450 µm, which is 90% of the height of the incision surface 110. In such an example, defects DE that are less than 450 µm in length may be acceptable, while defects that are greater than 450 µm in length may be unacceptable. However, the predetermined size in various embodiments is not limited thereto or thereby. In some embodiments, the height of the incision surface 100 may be the same as the height of the glass substrate 100.

As described above, in the method for detecting defects of the glass substrate according to some embodiments, the incision surfaces 110 of one or more transparent glass substrates 100 is subjected to plasma (PL) processing, and transparent defects DE formed on the incision surfaces 110 are visualized and compared to a predetermined size. In particular, the size of the defects DE displayed on the image IM is compared to the predetermined size, as determined by photographing the incision surface 110, to thereby determine the bending strength of the glass substrate 100. Accordingly, the glass substrate 100 may be classified as whether it can be used as the substrate of the display device, such as an organic light emitting diode display, a liquid crystal display, etc.

That is, as the transparent defects DE of the transparent glass substrate 100 is visualized by using the ions IO, the method of correctly detecting, measuring, and/or characterizing the defects DE of the glass substrate 100 is provided while determining the bending strength of the glass substrate 100.

Next, an experimental example confirming the effects of the method for detecting defects of the glass substrate according to some embodiments is described with reference to FIG. 4 to FIG. 6.

Figure 4:
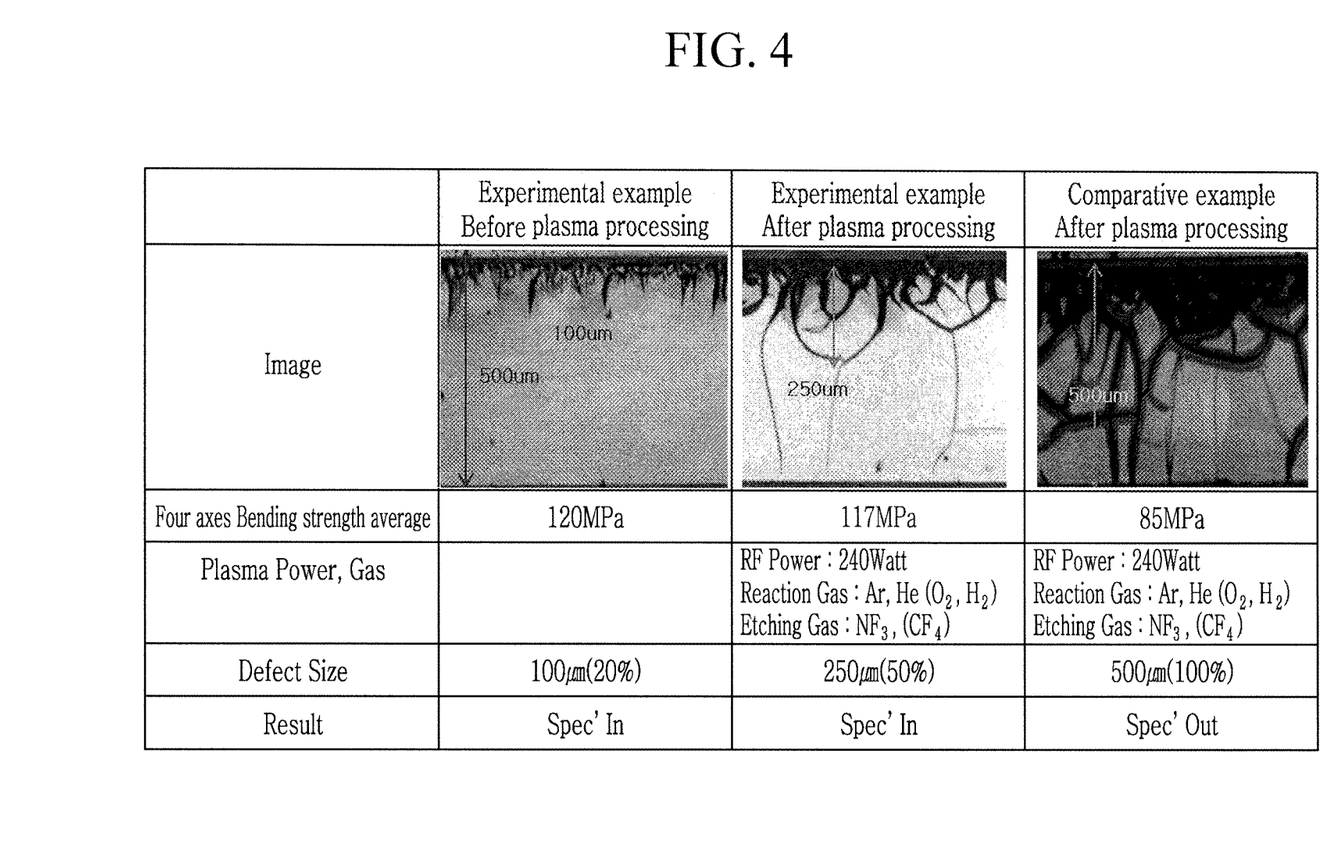
FIG. 4 is a table showing an experimental example and a comparative example.

FIG. 4 is a table showing an experimental example and a comparative example.

Referring to FIG. 4, each of the experimental example and the comparative example uses different glass substrates among a plurality of glass substrates cut from one glass mother substrate before plasma processing.

First, the incision surface of one glass substrate among the plurality of glass substrates is photographed before plasma processing. As shown in FIG. 4, the height of the incision surface of the glass substrate in the photographed image is 500 µm, while the size of the defect is depicted as being approximately 100 µm before plasma processing.

A four-axis (e.g., four-point) bending strength average of the plurality of glass substrates before the plasma processing is 120 megapascals (MPa).

Herein, the four-axis (e.g., four-point) bending strength may mean a maximum stress when the glass substrate is broken while being bent due to two-axis (e.g., two-point) pressure. In particular, a rear surface of the glass substrate is supported by two separated axes (e.g., the rear surface of the glass substrate is supported by two spaced apart points), and the two separated axes are pressed together to a center region of a front surface of the glass substrate (e.g., pressure is applied to the front surface of the glass substrate by two spaced apart axes or points while two additional spaced apart axes or points support or press against the rear surface of the glass substrate).

Also, the four-axis bending strength average may mean an average of the four-axis bending strength for the plurality of glass substrates.

Next, the incision surfaces of the plurality of glass substrates are plasma-processed. RF Power used in the plasma processing is 240 Watts, the reaction gas is argon (Ar) and helium (He) [or oxygen ($O_2$) and hydrogen ($H_2$)], and the etching gas is nitrogen trifluoride ($NF_3$) [or carbon tetrafluoride ($CF_4$)].

The defects of the incision surfaces of the plurality of glass substrates are visualized by the ion penetration by applying the plasma processing.

Next, the incision surfaces of the plurality of glass substrates are photographed to visualize the defects.

In the image of the incision surface of one glass substrate among the plurality of glass substrates according to the experimental example, the height of the incision surface of the glass substrate is 500 µm, and the size of the defect is approximately 250 µm. The four-axis bending strength average of the plurality of glass substrates after plasma processing according to the experimental example is 117 MPa.

In the image of the incision surface of one glass substrate among the plurality of glass substrates according to the comparative example, the height of the incision surface of the glass substrate is 500 µm, and the size of the defects are approximately 500 µm. The four-axis bending strength average of the plurality of glass substrates according to the comparative example is 85 MPa.

Figure 5:
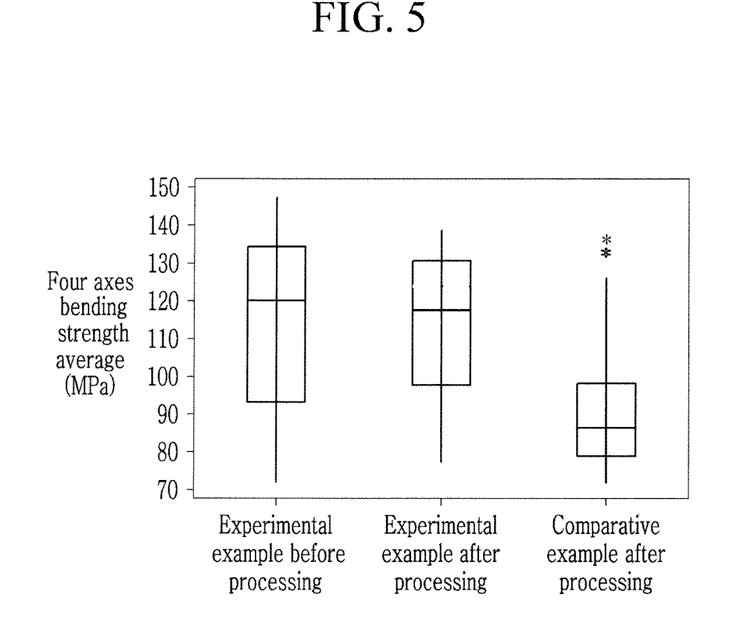
FIG. 5 is a graph showing a bending strength average of an experimental example and a comparative example.

FIG. 5 is a graph showing a bending strength average of an experimental example and a comparative example. FIG.

6 is a graph showing a percentage of a bending strength average of an experimental example and a comparative example.

Figure 6:
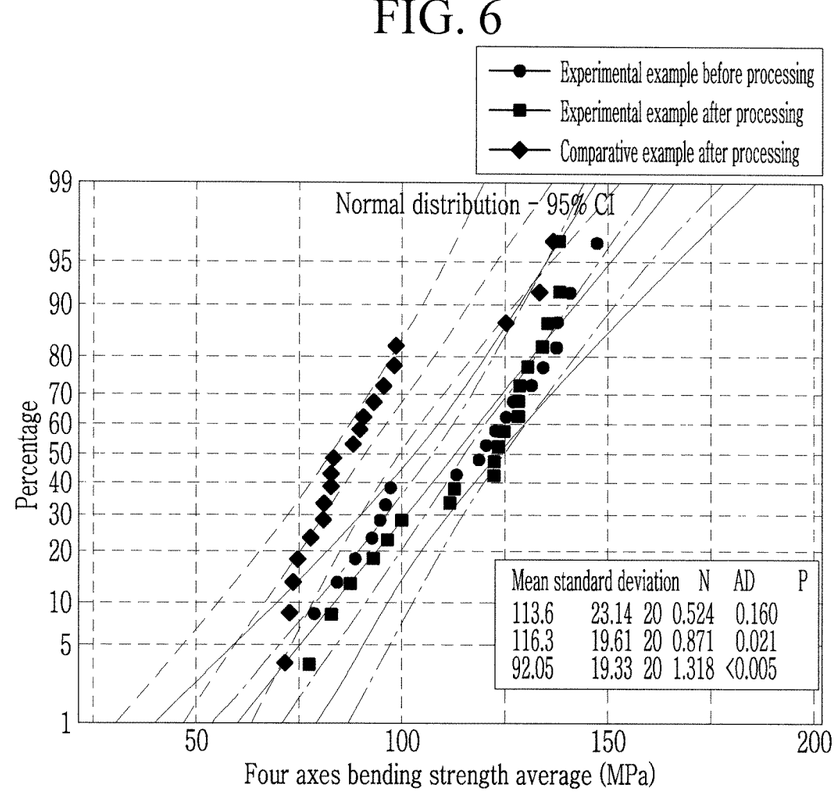
FIG. 6 is a graph showing a percentage of a bending strength average of an experimental example and a comparative example.

In FIGS. 4 to 6, the term "experimental example before processing" refers to a plurality of glass substrates before plasma processing, the term "experimental example after processing" refers to a plurality of glass substrates after plasma processing, and the term "comparative example after processing" refers to a comparative example after plasma processing.

FIG. 5 shows a depiction of the range of determined four-axis bending strength values, along with horizontal lines showing the average value. As depicted, the four-axis bending strength average is 120 MPa for the plurality of glass substrates before plasma processing, however the four-axis bending strength average is 117 MPa in the experimental example after plasma processing, and the four-axis bending strength average is 85 MPa in the comparative example after plasma processing.

Also, the size of the defect appears as 100 μm before plasma processing, which is 20% of the height of the incision surface for the plurality of glass substrates, however as the defects are visualized after plasma processing, the size of the defect is 250 μm, which is 50% of the height of the incision surface in the experimental example, and the size of the defects are 500 μm in the comparative example, which is 100% of the height of the incision surface.

As described above, in the experimental example as compared with the comparative example, the size of the incision surface of the glass substrate is smaller, and the four-axis bending strength average is higher.

Further, in the comparative example, the four-axis bending strength average is higher (e.g., greater) than a predetermined bending strength (e.g., 95 MPa) in the experimental example, and the four-axis bending strength is less than the predetermined bending strength in the comparative example. Accordingly, it may be determined that the glass substrate according to the experimental example is suitable (Spec' in) to be used as the substrate of the display device such as the organic light emitting diode display and the liquid crystal display, but the glass substrate according to the comparative example is not suitable (Spec' out) to be used as the substrate of the display device.

That is, as confirmed in the experimental example and the comparative example, the incision surfaces of the glass substrate of which the transparent defect is visualized through plasma processing are photographed, and the size of the defects in the images are determined and compared with the predetermined size. Accordingly, the bending strength of the glass substrates may be determined, thereby classifying whether the substrates are sufficient for use as the substrate of the display device. The glass substrate to be used as the substrate of the display device may be classified to be adoptive (i.e., sufficient for use as the substrate of the display device) or non-adoptive (i.e., not sufficient for use as the substrate of the display device).

As described above, as the transparent defects of the transparent glass substrate are visualized by applying the plasma processing to the incision surface of the glass substrate, the effect of the method of defecting the defects of the glass substrate is confirmed by determining the bending strength of the glass substrate.

Although example embodiments of the present invention have been described, it is understood that the present invention is not limited to these example embodiments, but various changes and modifications can be made by one of ordinary skill in the art within the spirit and scope of the present invention as hereinafter claimed.

Therefore, the disclosed subject matter is not be limited to any single embodiment described herein, and the above-described embodiments are to be considered illustrative and not restrictive. Accordingly, the scope of the present inventive concept shall be determined only according to the attached claims, and equivalents thereof.

What is claimed is:

1. A method for detecting defects of a glass substrate, the method comprising:
   cutting a glass mother substrate into a plurality of glass substrates and making incision surfaces to the plurality of glass substrates which are side surfaces of the plurality of glass substrates;
   penetrating ions into the incision surfaces of the plurality of glass substrates in perpendicular directions to the incision surfaces to visualize a defect of the incision surfaces; and
   photographing the defect of the incision surfaces to determine a bending strength of the glass substrate based on a size of the defect.

2. The detecting method of claim 1, wherein
   the step of visualizing the defect of the incision surfaces includes performing plasma processing on the incision surface.

3. The detecting method of claim 2, wherein
   the plasma processing is performed by using a mixture of a reaction gas and an etching gas.

4. The detecting method of claim 3, wherein
   the reaction gas comprises at least one from among argon (Ar), helium (He), oxygen ($O_2$), and hydrogen ($H_2$).

5. The detecting method of claim 3, wherein
   the etching gas comprises at least one of nitrogen trifluoride ($NF_3$) and carbon tetrafluoride ($CF_4$).

6. The detecting method of claim 2, wherein
   the plasma processing is performed for between 10 seconds and 10 minutes.

7. The detecting method of claim 2, wherein
   the plasma processing is performed after stacking the plurality of glass substrates.

8. The detecting method of claim 1, further comprising
   grinding the incision surfaces of the glass substrates after cutting the glass mother substrate into the plurality of glass substrates.

9. The detecting method of claim 1, wherein
   visualizing the defect of the incision surfaces is performed by blackening the defect through the ions.

10. The detecting method of claim 1, wherein
   determining the bending strength of the glass substrate based on the size of the defect is performed by using a photographed image of the incision surface.

* * * * *